(12) United States Patent
Kärkkäinen

(10) Patent No.: US 10,940,082 B2
(45) Date of Patent: Mar. 9, 2021

(54) METHOD AND ARRANGEMENT FOR ALLEVIATING THE STRESS-RELATED SLEEP DISORDER AND REDUCING THE STRESS LEVEL OF A PERSON

(71) Applicant: Oy Neurosonic Finland Ltd, Lahti (FI)

(72) Inventor: Marco Kärkkäinen, Lahti (FI)

(73) Assignee: Oy Neurosonic Finland Ltd, Lahti (FI)

( * ) Notice: Subject to any disclaimer, the term of this patent is extended or adjusted under 35 U.S.C. 154(b) by 1227 days.

(21) Appl. No.: 15/027,788

(22) PCT Filed: Oct. 6, 2014

(86) PCT No.: PCT/FI2014/050760
§ 371 (c)(1),
(2) Date: Apr. 7, 2016

(87) PCT Pub. No.: WO2015/052376
PCT Pub. Date: Apr. 16, 2015

(65) Prior Publication Data
US 2016/0242995 A1    Aug. 25, 2016

(30) Foreign Application Priority Data
Oct. 7, 2013   (FI) ........................... 20136002

(51) Int. Cl.
*A61H 23/02*   (2006.01)
*A61H 7/00*    (2006.01)
*A61B 5/024*   (2006.01)

(52) U.S. Cl.
CPC ............. *A61H 23/02* (2013.01); *A61B 5/024* (2013.01); *A61H 7/004* (2013.01);
(Continued)

(58) Field of Classification Search
CPC .... A61H 2201/5043; A61H 2201/5038; A61H 2201/5035; A61H 2201/5041;
(Continued)

(56) References Cited

U.S. PATENT DOCUMENTS 4,064,376 A * 12/1977 Yamada ............. A61H 23/0218
                                                    381/152
4,697,581 A * 10/1987 Endo .................. A61H 23/0218
                                                    310/29
(Continued)

FOREIGN PATENT DOCUMENTS

DE     3522305 A1    1/1986
EP     0417388 A2    3/1991
(Continued)

OTHER PUBLICATIONS

Maurice Ghaly and Dale Teplitz "The Biologic Effects of Grounding the Human Body During Sleep as Measured by Cortisol Levels and Subjective Reporting of Sleep, Pain, and Stress", Oct. 2004, Journal of Alternative and Complementary Medicine, vol. 10, pp. 767-776. (Year: 2004).*

(Continued)

*Primary Examiner* — Tu A Vo
*Assistant Examiner* — Alexander Morales
(74) *Attorney, Agent, or Firm* — Merchant & Gould P.C.

(57) ABSTRACT

A person's sleep disorders are resolved by applying low frequency vibration. Mechanical vibrators (1) present on a first side of a plate type base member (9) set the plate type base member (9) in vibration in such a way that its second surface transmits mechanical vibration. A plurality of first low frequency pulse trains (100; 101, 102, 103 . . . ) of mechanical vibration are conducted to a part of the person's body, at successive time periods (T; T1, T2, T3 . . . ). A frequency (f) of vibration in each individual pulse train (Continued)

(100) is maintained constant (f; fa, fb, fc . . . ) within the range of 20-50 Hz. The pressure pulses (400) of said pulse train (100) have a contact power (I) with said part of the body within the range of 40-70 dB. The constant frequencies (fa, fb, fc . . . ) of the successive pulse trains (100; 101, 102, 103 . . . ) are mutually different and change monotonously and mostly linearly. At least one second pulse train (100) is transmitted to said part of the body.

17 Claims, 7 Drawing Sheets

(52) U.S. Cl.
CPC . *A61H 23/0236* (2013.01); *A61H 2201/0142* (2013.01); *A61H 2201/0149* (2013.01); *A61H 2201/1604* (2013.01); *A61H 2201/164* (2013.01); *A61H 2201/1609* (2013.01); *A61H 2201/1623* (2013.01); *A61H 2201/5002* (2013.01); *A61H 2201/5035* (2013.01); *A61H 2201/5038* (2013.01); *A61H 2201/5041* (2013.01); *A61H 2201/5043* (2013.01); *A61H 2201/5097* (2013.01); *A61H 2205/02* (2013.01); *A61H 2205/04* (2013.01); *A61H 2205/062* (2013.01); *A61H 2205/081* (2013.01); *A61H 2205/106* (2013.01); *A61H 2205/108* (2013.01); *A61H 2230/06* (2013.01); *A61H 2230/30* (2013.01)

(58) Field of Classification Search
CPC .... A61H 2201/5097; A61H 2201/5002; A61H 2201/164; A61H 2201/0149; A61H 2201/1609; A61H 2201/0142; A61H 2201/1604; A61H 2201/1623; A61H 23/02; A61H 23/0236; A61H 7/004; A61H 2230/30; A61H 2230/06; A61H 2205/106; A61H 2205/062; A61H 2205/108; A61H 2205/04; A61H 2205/081; A61H 2205/02; A61H 1/001; A61H 2201/0138; A61M 2021/0022
USPC .......................................................... 600/26
See application file for complete search history.

(56) References Cited

U.S. PATENT DOCUMENTS

| | | | | |
|---|---|---|---|---|
| 5,076,260 | A * | 12/1991 | Komatsu | A47C 21/006 601/59 |
| 5,113,852 | A * | 5/1992 | Murtonen | A61H 23/0236 601/47 |
| 5,865,771 | A | 2/1999 | Shuto et al. | |
| 6,027,463 | A | 2/2000 | Moriyasu | |
| 6,102,846 | A * | 8/2000 | Patton | A61B 5/16 600/26 |
| 6,494,850 | B1 * | 12/2002 | Kitadou | A47C 3/02 601/49 |
| 6,505,361 | B1 * | 1/2003 | Ogawa | B06B 1/161 5/109 |
| 6,903,474 | B2 * | 6/2005 | An | H04R 9/066 310/15 |
| 7,442,174 | B2 * | 10/2008 | Butler | A61H 23/0236 601/15 |
| 9,949,004 | B2 * | 4/2018 | Cohen | A61H 23/0236 |
| 2003/0167026 | A1 * | 9/2003 | Tsujii | A61H 23/02 601/46 |
| 2004/0183343 | A1 * | 9/2004 | Probst | A61H 7/001 297/195.1 |
| 2007/0038164 | A1 * | 2/2007 | Afshar | A61H 23/0263 601/47 |
| 2008/0195007 | A1 | 8/2008 | Podrazhansky et al. | |
| 2011/0021866 | A1 * | 1/2011 | Iizuka | A61B 3/113 600/26 |

FOREIGN PATENT DOCUMENTS

| | | |
|---|---|---|
| EP | 0417388 B1 | 11/1994 |
| EP | 1325727 A2 | 7/2003 |
| WO | 9004379 A1 | 5/1990 |
| WO | 2005058144 A2 | 6/2005 |
| WO | WO 2006/048723 A1 | 11/2006 |
| WO | 2007137123 A2 | 11/2007 |
| WO | 2007137123 A3 | 12/2008 |
| WO | 2010043413 A1 | 4/2010 |
| WO | 2011042908 A1 | 4/2011 |

OTHER PUBLICATIONS

Majernik, Jaroslav, et al. Utilization of whole body vibration in therapy of patients with neurological disorders, International Conference on Digital Technologies, Confereence Proceeding Article, pp. 127-131, May 29, 2013 <DOI:10.1109/DT.2013.6566299>.
Finnish Patent and Registration Office Search report dated Jun. 6, 2014 for FI patent appln. No. 20136002.
Next Wave Ltd Physioacoustic. Physioacoustic chars. Retrieved from the Internet address http://fysioakustiikka.com/se/pdf/FA-product_2009.pdf.
Lappalainen T. Apua uni ei taaskaan tule. Retrieved Jun. 4, 2014 from the Internet address http://www.iltalehti.fi/terveys/200804017388315_tr.shtml, published on Apr. 1, 2008. Paragraph: Siniäantä ja tärinää.
Suomen Fysioakustiikka Oy. Hoitoa ja hyvää oloa äänivärähtelyllä. Retrieved from the Internet address http://fysioakustiikka.com/uutiset.htm.
Lähdetluoma, M. Tuoli hoitaa värähtelemällä. Yle Lahti, published on Oct. 17, 2011 (updated on Jun. 8, 2012) [retrieved on Jun. 4, 2014] from the Internet address http://yle.fi/uutiset/tuoli_hoitaa_varahtelemalla/5438427.
Haapaniemi, H. tutkimus Neurosonic-menetelmän vaikutuksesta stressiin ja unihäiriöiden hoitoon. Thesis, spring 2013, Education programme of Healthcare Technology, Oulu University of Applied Sciences. Published on Mar. 14, 2013.
Lappalainen, T. "Apua uni ei taaskaan tule". Retrieved on Jun. 4, 2014 from the Internet address: http://www.iltalehti.fi/terveys/200804017388315_tr.shtml, published on Apr. 1, 2008 Paragraph: Sine sound and vibration.
Suomen Fysioakustiikka Oy. "Hoitoa ja hyvää oloa äänivärähtelyllä". Retrieved from the Internet address: http://fysioakustiikka.com/uutiset.htm, whole publication, esp. News archive.
Lähdetluoma, M. "Tuoli hoitaa värähtelemällä". Yle Lahti. Published on Oct. 17, 2011 (dated Jun. 8, 2012) [Retrieved on Jun. 4, 2014], from the Internet address: http://yle.fi/uutiset/tuoli_hoitaa_varahtelemalla/5438427. Whole publication.
Haapaniemi, T. Tutkimus Neurosonic-menetelmän vaikutuksesta stressiin ja unihäiriöiden hoitoon. Thesis, spring 2013, Education progamme of Healthcare Technology, Oulu University of Applied Sciences. Published on Mar. 14, 2013.
European Patent Office, Supplementary European Search Report issued on EP14852936.5, dated May 8, 2017.

* cited by examiner

METHOD AND ARRANGEMENT FOR ALLEVIATING THE STRESS-RELATED SLEEP DISORDER AND REDUCING THE STRESS LEVEL OF A PERSON

CROSS-REFERENCE TO RELATED APPLICATION

This application is a national application of PCT-application PCT/FI2014/050760 filed on Oct. 6, 2014 and claiming priority of the Finnish national application number FI20136002 filed on Oct. 7, 2013, both of which are incorporated herein by reference.

FIELD OF THE INVENTION

The invention relates to a method for alleviating the stress-related sleep disorder of a person.

The invention relates also to a method for reducing the stress level of a person.

The invention further relates to an arrangement for alleviating the stress-related sleep disorder of a person.

The invention relates also to an arrangement for reducing the stress level of a person.

BACKGROUND

The prior art discloses a variety of equipment, wherein a seat or the like is fitted with mechanical vibrators capable of generating low frequency vibrations. Such a low frequency vibration has been said in the prior art to have a soothing and muscle-relaxing effect.

One such has been presented in the application publication WO 2006/048723, disclosing a vibration massage unit, wherein sound waves are first generated with an appropriate sound wave generator (10), the sound waves are then strengthened, and thereafter communicated to a sound converter (20) which converts the sound waves into mechanical vibrations through a resonant structure (1). The converter comprises preferably two distinct zones by means of which the sound is converted into vibrations within the range of 5-275 Hz and into vibrations within the range of 275-535 Hz.

The U.S. Pat. No. 5,865,771, in turn, discloses an incubator for newborn babies with an intention to generate low frequency vibration inside. The discussed low frequency vibration is produced with a sound signal generator and with a speaker amplifier coupled with the sound signal generator and connected to an electromechanical vibration transducer which filters from the sound a low frequency component to serve as vibrations. Such a low frequency vibration is said to help the newborn baby feel at ease and to prevent the experience of so-called bad dreams or nightmares.

However, the inventors have now discovered that the exactly specific type of low frequency vibration has surprisingly a stress-related sleep disorder alleviating and sleep quality improving effect. Based on this surprising discovery, it was a principal objective of the inventors to develop a method for generating a low frequency vibration and applying the same to parts of a body in such a way that the vibration would have an alleviating effect on stress-related sleep disorder.

Sleep disorders can be classified as follows (Duodecim):

Insomnia, alertness fluctuation, obstructive sleep apnea syndrome, restless legs syndrome, narcolepsy, parasomnia or special nocturnal disorders.

Another, older classification for sleep disorders (Duodecim) comprises sleep disorders causing a) insomnia, b) excessive daytime sleepiness, c) special nocturnal disorders or parasomnias and d) sleep problems associated with sleep-wake rhythm disorders such as jet lag and shift work.

In international sleep disorder classification (ICD-10), insomnia has been categorized in class F51.0 or G47.0, depending on the primary cause of insomnia.

The sleep disorder category F51.0 (insomnia) includes temporary and short-term adjustment insomnia (insomnia relating to changes in life, stress, and other emotional problems).

The same category F51.0 also includes long-term (psychophysiological) functional insomnia. The triggering cause of chronic functional insomnia can be stress, but the basic reason may also be some organic disease.

The insomnia category G47.0 includes long-term insomnias relating to functional disorders of the central nervous system.

Hence, regarding these sleep disorders of category F51.0, it is particularly the temporary adjustment insomnia (difficulties falling asleep) which is mainly stress related. Temporary insomnia resolves itself generally within a few days or weeks and is mainly associated with sensations of stress and anxiety or changes of environment.

In particular, the short-term functional adjustment insomnia of category F51.0 is caused by a determinable stress factor. The insomnia definable as adjustment insomnia lasts less than three months and involves emotional life-related factors as essential causes.

It is further notable in this context that the stress-related sleeplessness of a few nights in duration is not even rated as an actual categorizable sleep disorder and this is the most common cause of temporary and short-term insomnia (Partinen, Duodecim, Health Library).

Subsequently, this stress-related sleeplessness of a few nights in duration, which is not even classified as a sleep disorder, is indeed in this application referred to as "transient stress-related sleeplessness", when wishing to make specific reference thereto.

The most common source of long-term alertness fluctuation is sleep deprivation caused for example by shift work and so-called jet lag. In these sleep disorders the main cause of sleep deprivation may be traced to stress-related factors.

The sleep disorders from sleep-wake rhythm disturbances to jet lag are categorized in international sleep disorder classification (ICD-10) in class Z58.8 and the shift work sleep disorder in class G47.2.

On the other hand, the most common organic sleep disorder causing long-term fatigue is the sleep apnea syndrome. Another major source of long-term organic fatigue is narcolepsy.

Parasomnias are divided into four major groups, depending on whether they occur a) in waking-up phase (arousal disorders), b) during sleep-wake transitions, c) in REM sleep phase, or d) whether they are independent from stages of sleep. Typical parasomnias are, among others, sleep talking, nightmares, teeth grinding (bruxism), sleepwalking, nocturnal panic attacks, nocturnal enuresis and REM sleep behavior disorder. Prevention principles for attacks of parasomnia are similar to those applied for insomnia. Sufficient physical exercise is of paramount importance.

The most important type of sleep apnea is, on the other hand, obstructive sleep apnea caused by a blockage of the upper airways and, hence, its source is some organic disorder or disease. Sleep apnea is more than averagely common e.g. in those who suffer from hypertension, type 2 diabetes, and metabolic syndrome.

The restless legs syndrome is a sensomotoric neurological condition related to a dopamine system disorder of the central nervous system. Molecular biological studies have uncovered associations with genes regulating e.g. stored iron (ferritin) and regulating limb development. The scarcity of tissue iron impairs activity of the dopamine system. The restless legs syndrome is clearly more common in women than in men. The difference is a result of the scarcity of tissue iron lost during menstrual cycles and pregnancies. One reason for the decrease in tissue iron may also be attributed to repetitive blood donations.

The first symptom of narcolepsy is tiredness and tendency to nod off.

Emotional reactions, such as excitement or laughter, may trigger a cataplectic attack. In this event, the muscle tone suddenly disappears from some muscle group and the result is dropping of the jaw, collapse of the knees or dropping objects from the hands. Other less common symptoms include hypnagogic hallucinations and sleep paralyses. Narcolepsy patients have disorders in the hypocretin/orexin system.

In this application, the term of stress-related sleep disorders is mainly used in reference to stress-induced temporary short-term disturbances in the amount and quality of sleep. These include:
- temporary and short-term adjustment insomnia (less than 3 months), which in international sleep disorder classification is categorized in class F51.0,
- transient stress-related sleeplessness, which is included in adjustment insomnia and lasts a few nights;
- jet lag-related sleep disorders, which are categorized in international sleep disorder classification (ICD-10) in class Z58.8;
- shift work-related sleep disorders, which are categorized in international sleep disorder classification (ICD-10) in class G47.2;

The aforementioned stress-related sleep disorders are not associated with sleep disorders that have a background of organic defects or diseases (long-term i.e. chronic insomnia, sleep apnea, restless legs syndrome, narcolepsy, as is well as parasomnia i.e. nocturnal special disorders).

One important influence mechanism with regard to sleep and sleep disorders is through the activity and excessive secretion of GABA or gamma-aminobutyric acid. GABA suppresses activity of the brain and other central nervous system and sets the brain in a state of rest. GABA also inhibits the release of Cortisol (corticosteroid) or stress hormone from the adrenal cortex. The antigen of GABA is glutamate.

Melatonin ($C_{13}H_{16}N_2O_2$) or N-acetyl-5-methoxytryptamine is a "darkness hormone" found naturally in organism. In human body, it is secreted mainly by the pineal gland within the brain. The secretion of melatonin increases soon after dark, reaches its peak between 2 am and 4 am, and decreases towards the end of the night. Melatonin secretion is reduced if a person has stress or uses medicines acting like benzodiazepines (e.g. nod-off medicines) or beta blockers or alcohol. Melatonin has a molar mass of 232.28 g/mol and CAS-number_73-31-4. In terms of its chemical structure, melatonin resembles serotonin and, indeed, serotonin functions as a precursor of melatonin. The orally ingested melatonin does not have an effect on the body's serotonin levels.

Serotonin has an impact on the state of mind and its deficiency may manifest itself as melancholy, apathy, depression, and chronic fatigue. The shortage of serotonin may also lead to impulsive and violent behavior. Being a precursor of the darkness hormone melatonin, the deficiency of serotonin also affects sleep to some extent.

In terms of its chemical structure, serotonin is tryptamine like many psychotropic agents (psilocybin and DMT). Tryptophan ($C_{11}H_{12}N_2O_2$) is a precursor of serotonin. Serotonin works in the brain's pineal gland as an initiator for the synthesis of melatonin ($C_{13}H_{16}N_2O_2$).

From the standpoint of preventing transient sleep disorders, it is important that a person should sleep well and that the sleep cycle should contain recovering NREM sleep, thus precluding, among other things, the negative effects induced by stress.

The wellness (good feeling) enhancing effects of physical exercise have been explained by both psychological and physiological mechanisms. Psychological mechanisms include diversion (exercise takes one away from negative thoughts), mastery (learning and management of new physical skills), social contacts (especially in group activity), changes of psychological structures (self-image, self-esteem, capability) as well as changes in expectations and interpretation associated with physical exercise as the exercise increases. As for physiological mechanisms, the essential ones include increased concentrations of cerebral endorphins and monoamines (dopamine, serotonin, noradrenaline), hormonal activity of the hypothalamic-pituitary-adrenal axis (especially reduction in Cortisol secretion), neurotrophic growth factors and neuroplasticity. Likewise, the duration and quality of sleep may be improved, although these effects have been studied in more detail with non-depressed persons. Thus far, it is not clear whether the depressiveness-reducing effects of physical exercise can be partially attributed to the improvement of physical condition or fitness.

SUMMARY OF INVENTION

The inventors have now discovered that the method and arrangement of the invention are likely to have an effect similar to physical exercise, i.e. an increase in serotonin. This raises the level of melatonin and therefore a person falls asleep more easily and enjoys deeper and more rejuvenating sleep. In addition, one highly important aspect of the method and arrangement of the invention is the balancing of GABA secretion along with the decline of Cortisol secretion, which also contributes to the improvement of sleep quality.

More specifically, the inventors have now discovered that, when a person's body is subjected to the transmission of certain first low frequency vibrations which are relaxing and reassuring, and this is followed by supplying the same body part with low frequency vibrations which administer massage to the muscles, the result will be an effect that alleviates stress-related transient sleep disorders and thereby improves the quality of sleep.

It has been found that this vibration has first and foremost an increasing effect on the production of serotonin, melatonin and gamma-aminobutyric acid (GABA), and thereby contributes to decreasing the amount of stress-related hormones such as cortisol, histamine, acetylcholine, and noradrenaline.

The perception of stress is psychological and its psychic symptoms or stress sensations include, among other things, tenseness, crankiness, aggressions, restlessness, anxiety, memory problems, temporary sleep disorders (transient insomnia).

Since the perception of stress is subjective and is associated, among other things, with sensations of tenseness and anxiety experienced by a human being, the stress level can be measured e.g. by assessing the sensations and level of crankiness, tenseness, restlessness, etc. experienced by a person.

In this application, the low frequency mechanical vibration is a term used in reference to low frequency mechanical vibration of 20-50 Hz, which consists of longitudinal pressure pulses, such as sound waves, propagating in solid medium. When examining the effect of such vibration in a certain medium at a certain point x, each pulse of a pulse train has a certain duration t, during which time said pressure pulse has its amplitude fluctuating from zero to maximum amplitude. The observation point x in the present invention is a point at which the vibration makes contact with a person's body part.

Amplitude refers here to the difference $dp=p1-p2$ of vibratory pressure p1 at a certain point x in the medium, wherein p2 is the pressure of undisturbed air mass. Preferably, such a pulse train consists of successive sinusoidal pulses (waves) capable of being more or less presented with an equation:

$$A(x,t)=A \max \sin(kx-wt+o) \quad (1)$$

wherein Amax represents the maximum amplitude of a pulse, i.e. the maximum pressure difference dpmax as compared to the pressure of undisturbed air mass,
$A(x,t)$ represents the vibratory pressure of a pulse presently at a propagation point x with respect to the pressure of undisturbed air mass at a time point t,
k is the number of waves,
w is rotational frequency
o is phase constant.

The invention relates to a method for the treatment of a person's stress-related sleep disorders.

More specifically, the invention relates to a method for alleviating a person's stress-related sleep disorder, particularly for alleviating stress-related transient adjustment insomnia, which comprises applying low frequency vibration to a part of the body with an apparatus which includes a plate type base member capable of having brought to contact therewith mechanical vibrators by which said base member can be set in vibration. The method comprises
A) detecting a sleep disorder related to a person's stress level, especially stress-related transient insomnia, by assessing or measuring,
B) using mechanical vibrators (1) present on a first side of the apparatus' plate type base member for setting the plate type base member in vibration in such a way that one of its surfaces transmits mechanical vibration, comprising a plurality of low frequency pulse trains which are conveyed to a person's body or selected body part. The successive mechanical vibration pulse trains to be transmitted to the body or a specific part of the body comprise
  a first vibration component, which consists of a plurality of first successive pulse trains or vibration cycles transmitted at successive time periods (T; T1, T2, T3 . . . ) to the body or said part of the body, each of said pulse trains having a duration (T; T1, T2, T3 . . . ) of several minutes and a frequency (f; fa, fb, fc) of the vibration being constant within the range of 20-50 Hz through said duration of the pulse train, while an amplitude A of the vibration, i.e. the pressure difference of each (pressure) pulse with respect to undisturbed air mass, is at the same time adapted to be such that pressure pulses (400) included in each pulse train have a contact power with the body or said body part within the range of 40-70 dB, whereby the constant frequencies (fa, fb, fc . . . ) of successive pulse trains are mutually different and change monotonously and mostly linearly when proceeding from a first vibration cycle to a second one; and further
  a second vibration component, which consists of at least one second pulse train or second vibration cycle transmitted to the body or said part of the body, wherein the pressure pulses included in a pulse train (100) have a frequency (f) fluctuating within the range of 20-50 Hz, preferably within the range of 20-40 Hz, over the course of 2-10 seconds, preferably over the course of 5-7 seconds, and said frequency of pressure pulses changes in accordance with sine, triangle or square wave, preferably in accordance with sine wave,
C) measuring or assessing a stress level associated with the stress-related sleep disorder and deciding, on the basis of the measured or detected stress level, whether the treatment is continued again from step A.

The selected body part refers here to a single part of the body, such as calves, thighs, back, neck, shoulders, lower limbs, upper limbs, etc., i.e. various parts of the body.

The contact power of pressure pulses with the body or a selected part of the body, such as with calves, upper limbs, etc., refers to power, measured in decibels, with which the pressure pulses included in low frequency vibration come to contact with a person's body or body part.

The stress-related sleep disorder is a term used specifically in reference to a stress-related transient insomnia, which is not caused by an organic disorder or disease such as sleep apnea.

Hence, the stress-related sleep disorder has been selected from a group consisting of
  temporary and short-term adjustment insomnia (less than 3 months), which in international sleep disorder classification has been categorized in class F51.0,
  transient stress-related sleeplessness, which is included in adjustment insomnia and which lasts a few nights;
  jet lag-related sleep disorders, which in international sleep disorder classification (ICD-0) have been categorized in class Z58.8 and
  shift work-related sleep disorders, which in international sleep disorder classification (ICD-10) have been categorized in class G47.2.

On the other hand, the method for reducing a person's stress comprises applying low frequency vibration to the body or to at least one part of the body with an apparatus which includes a plate type base member capable of having brought to contact therewith mechanical vibrators by which said base member can be set in vibration. The method comprises
A) detecting a person's stress level by assessing or measuring,
B) using mechanical vibrators present on a first side of the apparatus' plate type base member for setting the plate type base member in vibration in such a way that one of its surfaces transmits mechanical vibration, comprising a plurality of low frequency pulse trains which are conducted to a person's body or selected body part. The successive mechanical vibration pulse trains to be transmitted to the body or a specific part of the body comprise
  a first vibration component, which consists of a plurality of first successive pulse trains or vibration cycles transmitted at successive time periods (T; T1, T2, T3 . . . ) to the body or a selected part of the body, each of said pulse trains having a duration (T; T1, T2, T3 . . . ) of several minutes and a frequency (f; fa, fb, fc) of the vibration being constant within the range of 20-50 Hz through said duration of the pulse train, while the vibration is at the same time adapted to be such that pressure pulses included in each pulse train have a contact power with the body or said body part within the range of 40-70 dB, whereby the constant frequencies of successive pulse trains are mutually different and change monotonously and mostly linearly when proceeding from a first vibration cycle to a second one; and further a second vibration component, which consists of at least one second pulse train or second vibration cycle transmitted to the body or said part of the body, wherein the pressure pulses included in a pulse train have a frequency fluctuating within the range of 20-50 Hz, preferably within the range of 20-40 Hz, over the course of 2-10 seconds, preferably over the course of 5-7 seconds, and said frequency of pressure pulses changes in accordance with sine, triangle or square wave, preferably in accordance with sine wave, C) detecting a stress level and deciding, on the basis of the measured or assessed stress level, whether the treatment is continued again from step A.

In one embodiment of the invention, the stress level is measured by measuring a person's heart rate, especially morning heart rate.

In another embodiment of the invention, the stress level is detected by assessing a person's stress sensations for example by means of a written evaluation form.

In yet another preferred embodiment of the invention, the stress level is observed by measuring the amount of hormones associated with elevated stress level, particularly the amount of noradrenaline, serotonin, dopamine, melatonin, cortisol, histamine or gamma-aminobutyric acid (GABA).

In the invention, the frequency of vibration in the first vibration component remains always constant throughout the duration of a vibration cycle (pulse train), while the amplitude of vibration fluctuates in keeping with the sine wave within the range of 0-Am. With regard to the plurality of successive vibration cycles, which collectively constitute said first vibration component, the frequency of vibration remains constant always throughout a single vibration cycle, but changes between successive vibration cycles monotonously, i.e. in the same direction. Preferably, the frequency of vibration changes linearly, i.e. the constant frequency decreases or increases always by the same amount between successive vibration cycles. When the body is subjected to such static pulse trains of mechanical vibration, the vibration is perceived as particularly reassuring.

After the body/body part has for a certain time been subjected to the first vibration component, which comprises vibration that remains constant in terms of its frequency throughout each vibration cycle of the vibration component, the body/body part is thereafter subjected to a second vibration component, which comprises muscle-toning low frequency vibration. In this second vibration component, in which the frequency of vibration changes, the maximum amplitude of vibration, i.e. the highest pressure generated by the vibration in air mass at a certain point of the air mass, remains preferably constant. In this second vibration component, the frequency of vibration changes over the course of 2-10 seconds while the frequency of vibration fluctuates within the range of 20-50 Hz, preferably within the range of 20-40 Hz, and the frequency of vibration changes preferably in compliance with the sine wave.

In a preferred embodiment of the invention, the successive pressure pulse trains included in each vibration cycle of the first vibration component consist of steady-state frequency longitudinal vibration, such as a sound, wherein the pulses of a pulse train are made up by pressure waves whose contact power with the body part lies within the range of 40-70 dB, preferably 40-70 dB.

In a second preferred embodiment of the invention, the difference between constant frequencies (f) of the successive pulse trains included in each vibration cycle of the first vibration component remains always the same and is preferably 1-4 Hz.

In yet another embodiment of the invention, the frequency (f) of pressure pulses included in each vibration cycle of the second vibration component fluctuates within the range of 20-50 Hz, preferably within the range of 20-40 Hz, and the frequency changes in compliance with sine, triangle or square wave, preferably in compliance with sine wave. Throughout the duration t of each pressure pulse, the amplitude pulse made up by the maximum pressures of pressure pulses is preferably square or sinusoidal in shape, whereby the amplitude pulse made up by the maximum pressures of pressure pulses has a duration of about 1-2 seconds. Preferably, at the frequency of each pressure pulse of a pulse train, the contact power of a pressure pulse with a person's body lies within the range of 40-70 dB, preferably within the range of 57-64 dB.

The duration t of a single (pressure) pulse refers here to a time period during which the pressure (p) of vibration changes over the sequence of pmin–pmax–pmin.

The invention relates also to an arrangement for alleviating a person's stress-related sleep disorder, especially for alleviating stress-related transient adjustment insomnia with an apparatus which comprises a plurality of vibrator elements, mounted one or more of the apparatus' solid or flexible resonatable base members and capable of converting an electrical impulse into a pulse of mechanical vibration, as well as a data processing unit with a capability of producing a control instruction for setting up an electrical impulse train by using the mechanical vibrators present on a first side of the apparatus, i.e. on an opposite side of the base member with respect to the person's body, for setting the base member to vibrate in resonance with said mechanical vibrators in such a way that the base member's second surface, which is opposite to said first side and closer to the person's body, transmits to the body or to a selected part of the body low frequency mechanical vibration consisting of successive pressure pulses of mechanical vibration. The pressure pulses make up a first vibration component, which comprises a plurality of first successive reassuring vibration cycles comprising low frequency successive pressure pulses, and a second vibration component to be transmitted thereafter and comprising at least one second massaging vibration cycle. Thus, there is a first vibration component, which comprises a plurality of successive soothing vibration cycles transmitted to the body or said part of the body at successive time periods (T; T1, T2, T3 . . . ), which comprises low frequency successive pressure pulses, each pulse train of which has a duration (T; T1, T2, T3 . . . ) of several minutes and a vibration frequency (f; fa, fb, fc.) which is constant within the range of 20-50 Hz through said duration of the pulse train, while (pressure) pulses (400) of the vibration are at the same time adapted to be such that pressure pulses included in each pulse train have a contact power (I) with said body part within the range of 40-70 dB, and a second vibration component, which is transmitted thereafter to the body or to said part of the body and which comprises at least one second massaging vibration cycle, the pressure pulses included in said one second vibration component having a frequency (f) fluctuating within the range of 20-50 Hz, preferably within the range of 20-40 Hz, over the course of 2-10 seconds, preferably over the course of 5-7 seconds, and said frequency of pressure pulses changes in accordance with sine, triangle or square wave, preferably in accordance with sine wave.

In one preferred embodiment of the invention, the apparatus consists of a bed or chair, whereby vibrator elements mounted on solid or flexible base members of its plate type base are located within a frame of the chair or bed, and mechanical vibrations generated by the vibrator elements are adapted to be conducted, by way of a medium made of leather and/or cushioning, to that part of a person's body desired to have vibration applied thereto.

Preferably, the chair includes a back and a two-piece seat, comprising a first upper seat component adapted to support an upper part of the legs and having preferably an approximately horizontal orientation, as well as a second seat component adapted to support a lower part of the legs and having its longitudinal direction at an angle relative to the longitudinal direction of the first seat component, whereby inside the back, the lower seat component and the upper seat component of the chair extends a discontinuous stiff plate type base whose base members, located in the back, in the lower seat component and in the upper seat component, have embedded therein vibrator elements converting electronic vibration into mechanical one.

The data processing unit includes preferably a user interface, a central processing unit, as well as means for setting up a signal pulse train on the basis of instructions given by the user. Preferably, the data processing unit is adapted to generate, as a control instruction, a signal pulse train by means of an oscillator.

The invention relates also to a piece of software installed in the data processing unit, which is adapted to set up by means of the central processing unit, as a control instruction, a signal pulse train which enables the development of the aforesaid plurality of mechanical low frequency pulse trains comprising first and second vibration components.

BRIEF DESCRIPTION OF THE DRAWINGS

The invention will now be described in more detail with reference to the accompanying figures.

DESCRIPTION OF THE PREFERRED EMBODIMENTS

FIGS. 1A to 10 illustrate vibration cycles 1000 comprising amplitude pulses as well as a frequency f for pulse trains in vibration cycles 100 in both reassuring vibration cycles 1000 and muscle-toning second vibration cycles of longitudinal mechanical vibration generated in the invention.

The mechanical pulse always involves a certain change of amplitude A in the vibration pressure P of mechanical vibration over the course of a certain pulse duration t. The pulse duration is here perceived as a time period between the respective points of two successive pressure pulses, e.g. a lapse of time from the peak of a preceding pulse to the peak of a subsequent one.

Figure 1A:
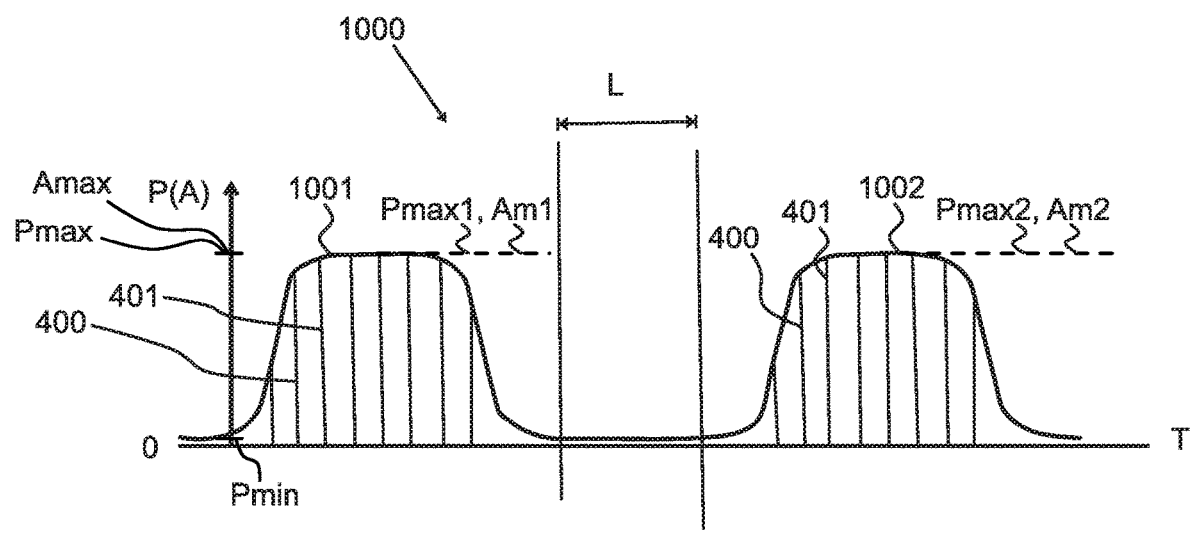
FIG. 1A illustrates the formation of a pulse train containing mechanical pulses.

It is visible in FIG. 1A how the pulse train of each first vibration cycle 1000 comprises longitudinal vibration made up by successive pressure fluctuations in a medium (a solid substance capable conducting pressure waves). The successive densifications and sparsifications of the medium constitute a source of pressure pulses (waves), wherein a single wave or pressure pulse 400 develops always between points present at the same phase of a pressure wave. In FIG. 1A there is visible a pressure pulse 400; 401 which develops between two pressure maxima.

The vibration pressure P in a single pressure pulse 400; 401 fluctuates in the range of Pmin–Pmax, wherein Pmin is the air pressure of an undisturbed medium such as air mass.

Thus, the amplitude A over a single pressure pulse 400; 401 fluctuates in the range of 0–Amax, wherein Amax is a maximum amplitude corresponding to a maximum pressure difference Pmax–Pmin of the pressure pulse.

The invention, both in the first vibration component and in the second vibration component of vibration, comprises modulating the pulse train (pressure wave) of mechanical vibration in such a way that the maximum amplitude Amax, which matches the maximum pressures Pmax of the successive pressure pulses 400 in pulse trains included in the first vibration component or a vibration cycle 1000 or in the second vibration cycle 100, changes from a pressure pulse to the next during a vibration component of the vibration cycle 1000, producing thereby an amplitude pulse whose maximum amplitude is Am. The amplitude pulse is preferably in the shape of a sine wave, whereby it rises over a certain time period from zero to its maximum value Am and back to zero (the zero naturally means that there are no pressure pulses).

In FIG. 1A there is visible the development of the maximum amplitude Am for amplitude pulses in two successive vibration cycles 1000; 1001 and 1000; 1002 of the first vibration component (sleep cycle). The maximum amplitudes A for the successive pressure pulses 400 of the first vibration component's vibration cycle 1000; 1001, 1002 start from zero, rise always during a certain time period to a maximum value thereof, and fall back to zero. In the invention, the maximum amplitudes of the successive first vibration components' pressure pulses develop an amplitude pulse, which propagates in the shape of a sine curve and whose maximum amplitude is Am. The maximum amplitudes Am of amplitude pulses have values which are either equal in the same phase of a vibration component, i.e. Ami=Am2, or usually fluctuate from one vibration cycle to the next Ami=/Am2. The duration of each amplitude pulse 400 is about 10-15 s in the first vibration component as well as in the second vibration component.

Figure 1B:
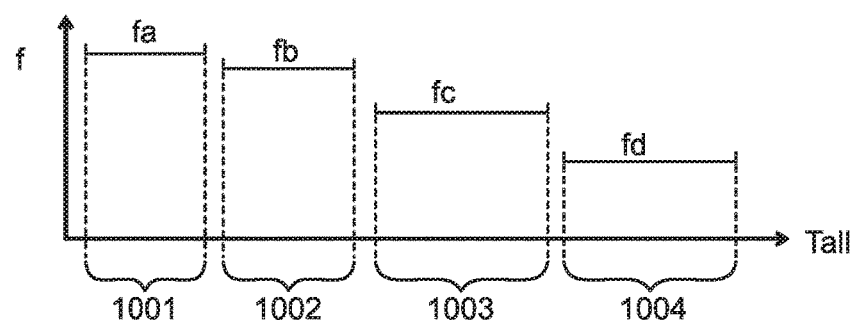
FIG. 1B illustrates frequency modulation of a pulse train containing mechanical pulses.
Figure 1C:
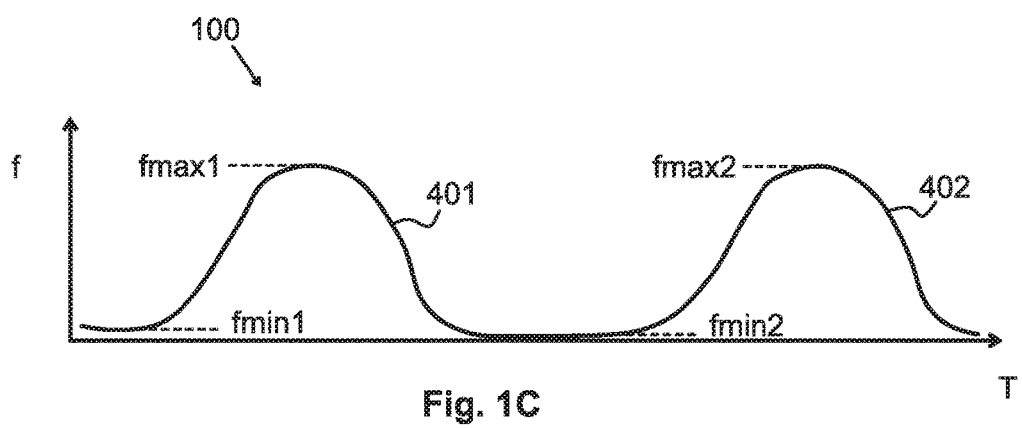
FIG. 1C illustrates amplitude modulation of a pulse train containing mechanical pulses.

In FIG. 1B, on the other hand, there is depicted how the vibration frequency f in the first vibration component of mechanical vibration to be transmitted to a body always remains constant during each vibration cycle. The aggregate time of vibration cycles is Tall. Each vibration cycle 1000 consists of a pulse train. The figure shows four vibration cycles 1000; 1001, 1000; 1002, 1000; 1003 and 1000; 1004 during each of which the vibration frequency f remains constant fa, fb, fc and fd. However, the constant frequency of vibration changes when proceeding from a vibration cycle to the next. The change occurs mainly in a linear fashion, i.e. the constant frequency fa, fab, fac . . . changes between vibration cycles always by the same amount either up or down.

In FIG. 10 there is further visible how the vibration frequency f, during a second vibration component arriving at the body, changes over a duration T of each pressure pulse of the second vibration component 100 in the shape of a sine curve within the range of fmin–fmax, wherein fmax is fmax1 or fmax2 when the maximum amplitude Am of vibration differs from zero. The maximum frequency fmax fluctuates over the duration T of a pulse train of the second vibration component within the range of 20-50 Hz, preferably within the range of 23-38 Hz, such as for example within the range of 23-33 Hz or 32-38 Hz.

Between successive pulses of the pulse train in a vibration cycle 1000; 1001, 1002 . . . or 100; 101, 102 . . . there is often a short pause whose duration is L (if pulses have a length which is very short, in the order of a few seconds, the pause between pulses is often omitted).

Figure 2A:
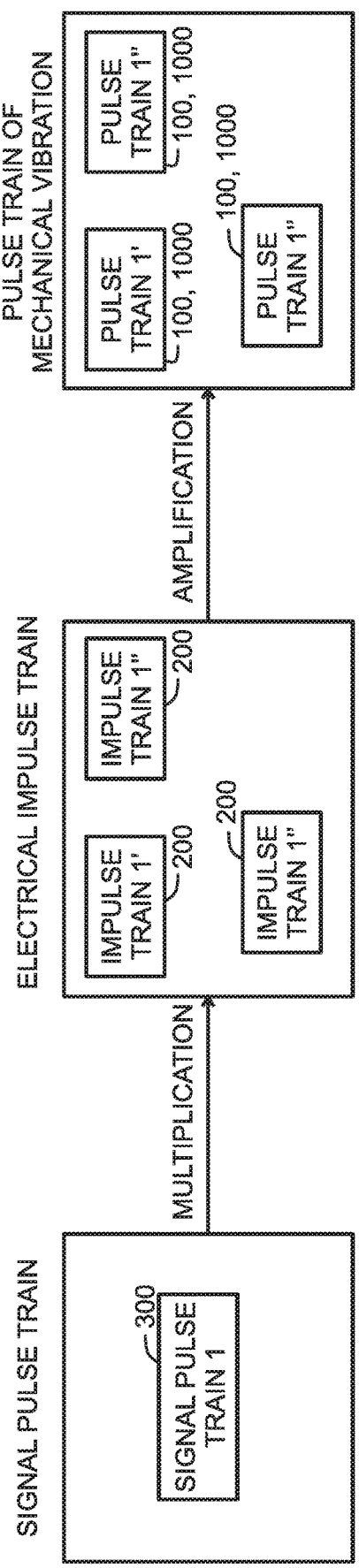
FIG. 2A shows a principle for constructing a signal pulse train, an electrical pulse train, and a mechanical pulse train.

FIG. 2 shows in a simplified diagram view how a pulse train in a vibration cycle 100 of mechanical vibration to be transmitted to a certain part of the body develops in an apparatus of the invention. It has been illustrated in the figure how each signal pulse train 300 (signal pulse train 1), transmitted from a data processing unit, is first converted into three identical electrical impulse trains 200 (impulse train 1', impulse train 1", and impulse train 1''') with a signal card, each of those being then converted into respective pulse trains in vibration cycles 100 or 1000 of mechanical vibration (pulse train 1', pulse train 1", and pulse train 1''') with three vibrator elements. It is obvious for a skilled artisan that, with minor modifications of the apparatus, from each signal pulse train 300 can be constructed impulse trains 200 and thereby also pulse trains 100 of mechanical vibration in larger or smaller numbers than what is shown in FIG. 2A.

In practice, an apparatus 10 of the invention is capable of producing with vibrator element 1 simultaneously generally 1 and not more than 2 different vibration components or vibration cycles 1000 or 100 of mechanical vibration. The pressure pulses containing mechanical vibration are conducted from the vibrator elements 1 by way of a solid object to various types of muscles, such as to major muscles/muscle groups as well as to minor muscles/muscle groups, each time by the action of 3, 6 or 9 vibrator elements.

Figure 2B:
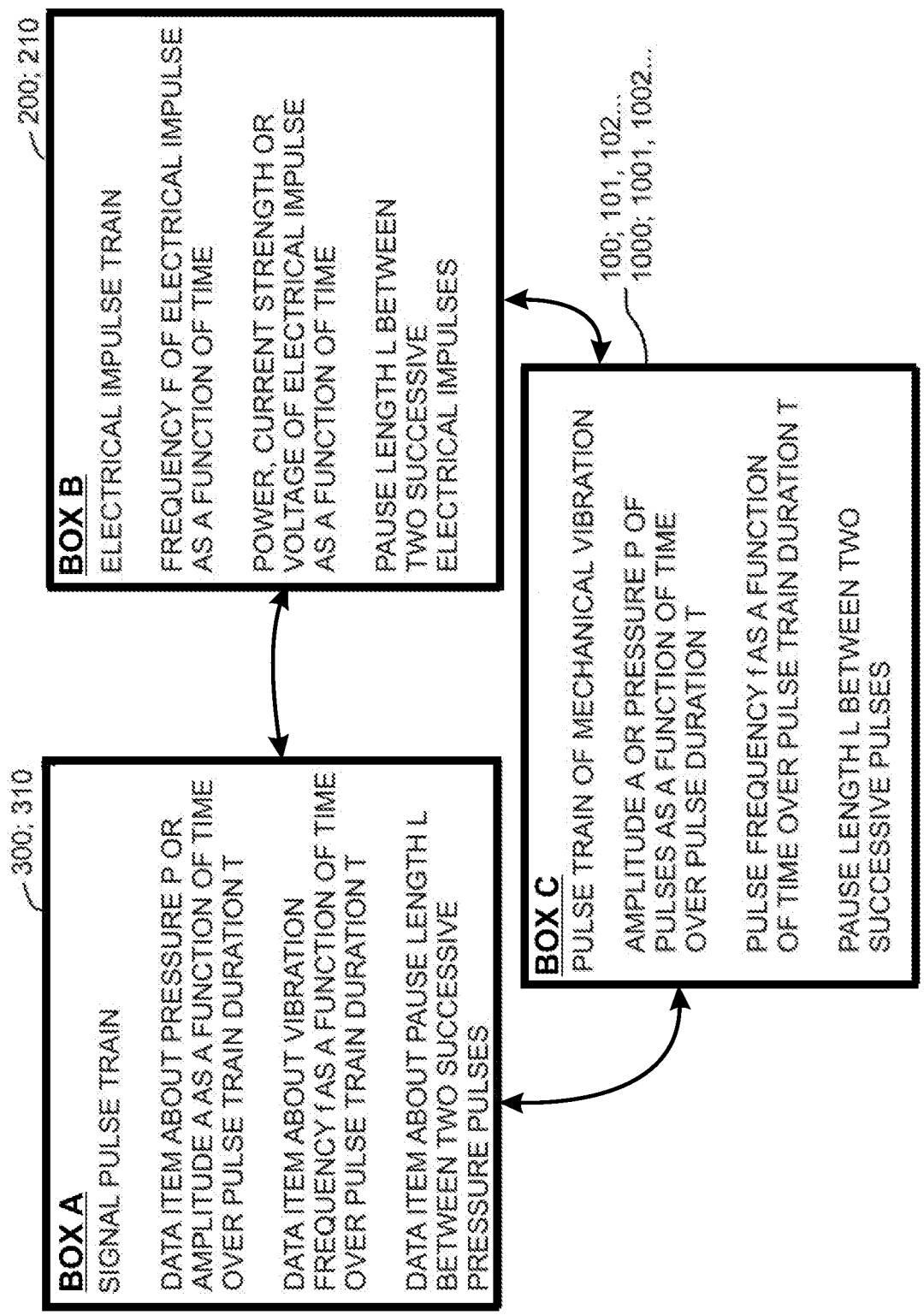
FIG. 2B shows in a diagram the data/quantities required for constructing a signal pulse train in Box A, an electrical impulse train in Box B, and a pulse train of mechanical vibration in Box C.

Next will be described more precisely, with reference to FIGS. 2A, 2B, as well as 3, how the apparatus of the invention is used for creating a signal pulse train 300, an impulse train 200, as well as a respective vibration component 100 or 1000 (a train of successive pressure pulses). As shown in FIGS. 2A and 2B, the certain vibration component or vibration cycle 100 or 1000 of mechanical vibration, which comprises a plurality of successive vibration cycles 101, 102, 102 . . . or 1001, 1002 . . . , is based on a signal pulse train 300 to be established with a data processing unit 5 as a control instruction. The data contained in this signal pulse train 300 is used as a basis for generating respective electrical impulse trains 200 which are distributed by way of a signal board (board in general 4; signal board 41) and an amplifier board (board in general 4; amplifier board 42) (cf. FIG. 4A) to appropriate vibrator elements 1 for a conversion into mechanical vibration.

Hence, an individual signal pulse 310 in the signal pulse train 300 established by the data processing unit 5 comprises, as presented in FIG. 2B, comprises a data item about the duration of each signal pulse included in this particular signal pulse train 300 and a data item about how the amplitude A (or vibration pressure P) of a pressure pulse 400 of mechanical vibration is desired to change over the duration T of each vibration cycle 100, 101 . . . or 1001, 1002 . . . . In addition, the signal pulse train 300 contains a data item about the length L of a pause between two successive signal pulses 310 included in the pulse train.

The signal pulse train 300 generated by the data processing unit 5 will be thereafter converted and multiplied, for example by means of a signal board 41 and amplifier boards 42 coupled therewith, into a plurality of identical amplified impulse trains 200. It is the amplification magnitude of the signal pulse train 300 which determines first the amplitude modulation for the impulse train 200 and thereafter the development regarding the maximum amplitude Am for the amplitude pulses of each vibration cycle (pulse train) 100; 101, 102 . . . or 1000; 1001, 1002 . . . of mechanical vibration generated from the impulse trains (cf. FIG. 1). The number of generated, amplified analog or preferably digital impulse trains 200 matches the number of mechanical vibrators 1 in the apparatus.

Thus, each impulse train 200 has a certain duration over which the frequency F of an impulse 210 and the electric field strength or electric field properties directly proportional thereto (e.g. current, voltage) of each impulse train 200 will change in such a way that, over the duration of the impulse 210, there are obtained respective vibration cycles which are changing in a desired manner and are made up by the pressure pulses 400 of a respective vibration component or vibration cycle 100 or 1000 of mechanical vibration.

Hence, the changes of frequency F in each electrical impulse train 200 are matched by the changes of frequency f in the vibration cycles (mechanical pulse trains) 101, 102 . . . or 1001, 1002 . . . of the mechanical vibration components and the changes of electric field (I, U, P) in the analog or preferably digital impulse 210 are matched by the changes of amplitude A (or vibration pressure P) in the mechanical pulse train (vibration cycle) 100; 101, 102 . . . or 1000; 1001, 1002 . . . . In a preferred embodiment of the invention, the signal pulse train 300, the impulse train 200, as well as the vibration cycles 100; 101, 102 . . . or 1000; 1001, 1002 . . . of the vibration component of mechanical vibration, comprise not only the duration of each pressure pulse but also a data item about delay time L between two successive pressure pulses 400; 401, 402.

Figure 3:
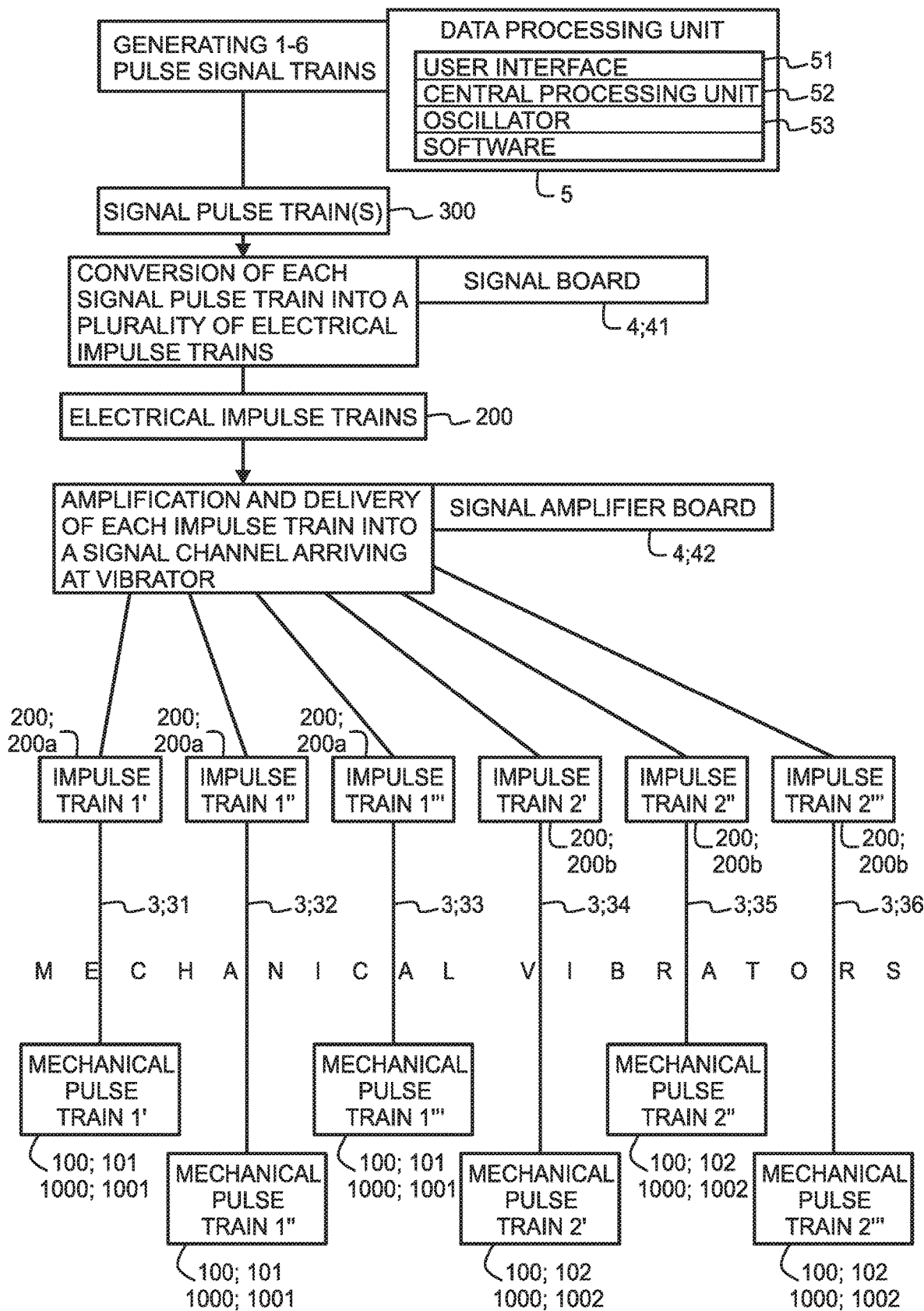
FIG. 3 shows in a diagram the formation of a mechanical pulse train in an apparatus of the invention by using a method of the invention.

It is explained in more detail with FIG. 3 as well as 4A-4C how the above roughly described vibration component or vibration cycle 100 or 1000 of mechanical vibration is brought about by one apparatus 10 of the invention (a chair fitted with vibrator elements and a data processing unit controlling operation of the vibrator elements).

Figure 4A:
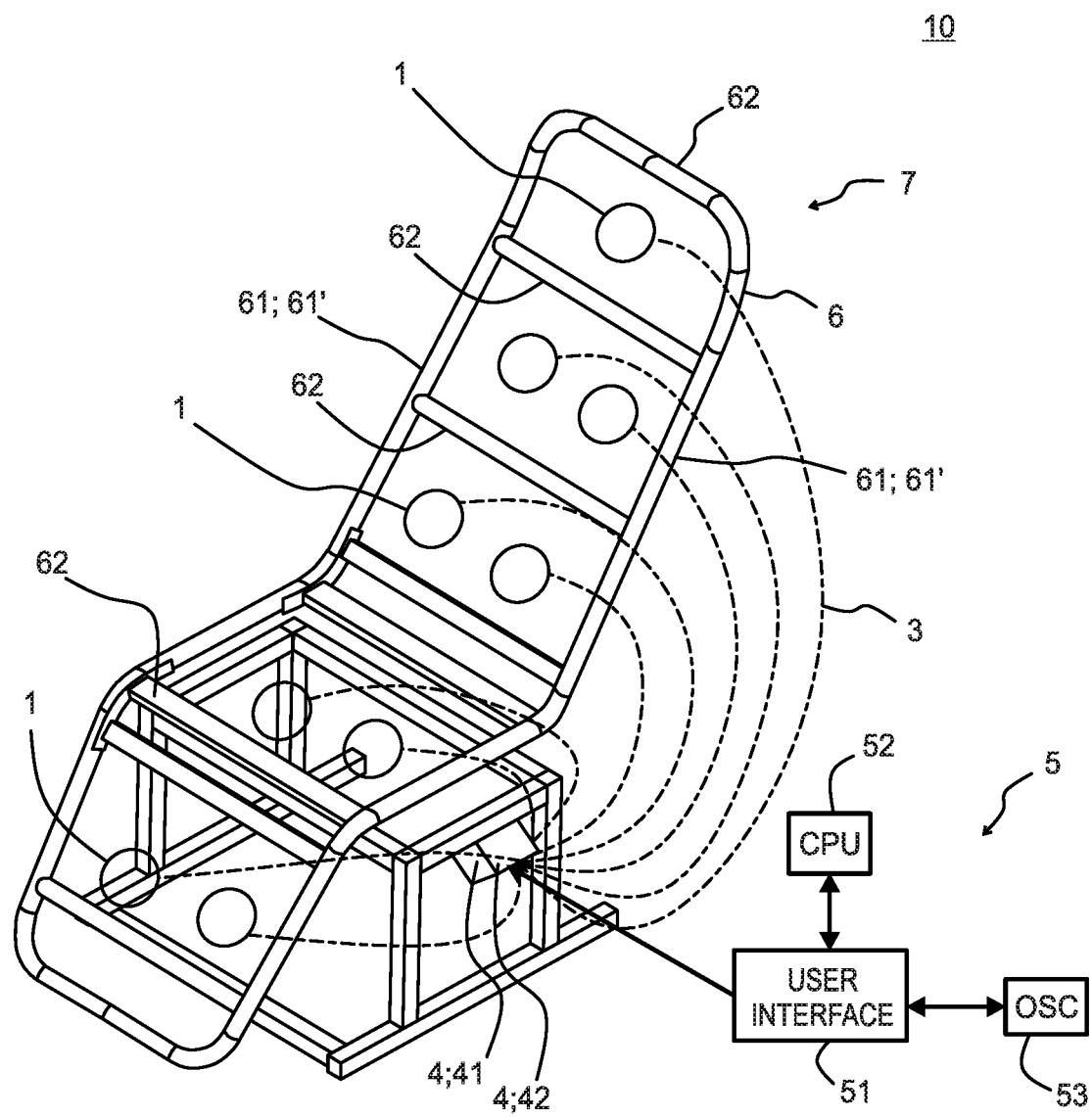
FIG. 4A visualizes schematically a chair according to one exemplary embodiment of the invention, which is fitted with means for generating mechanical vibration.
Figure 4B:
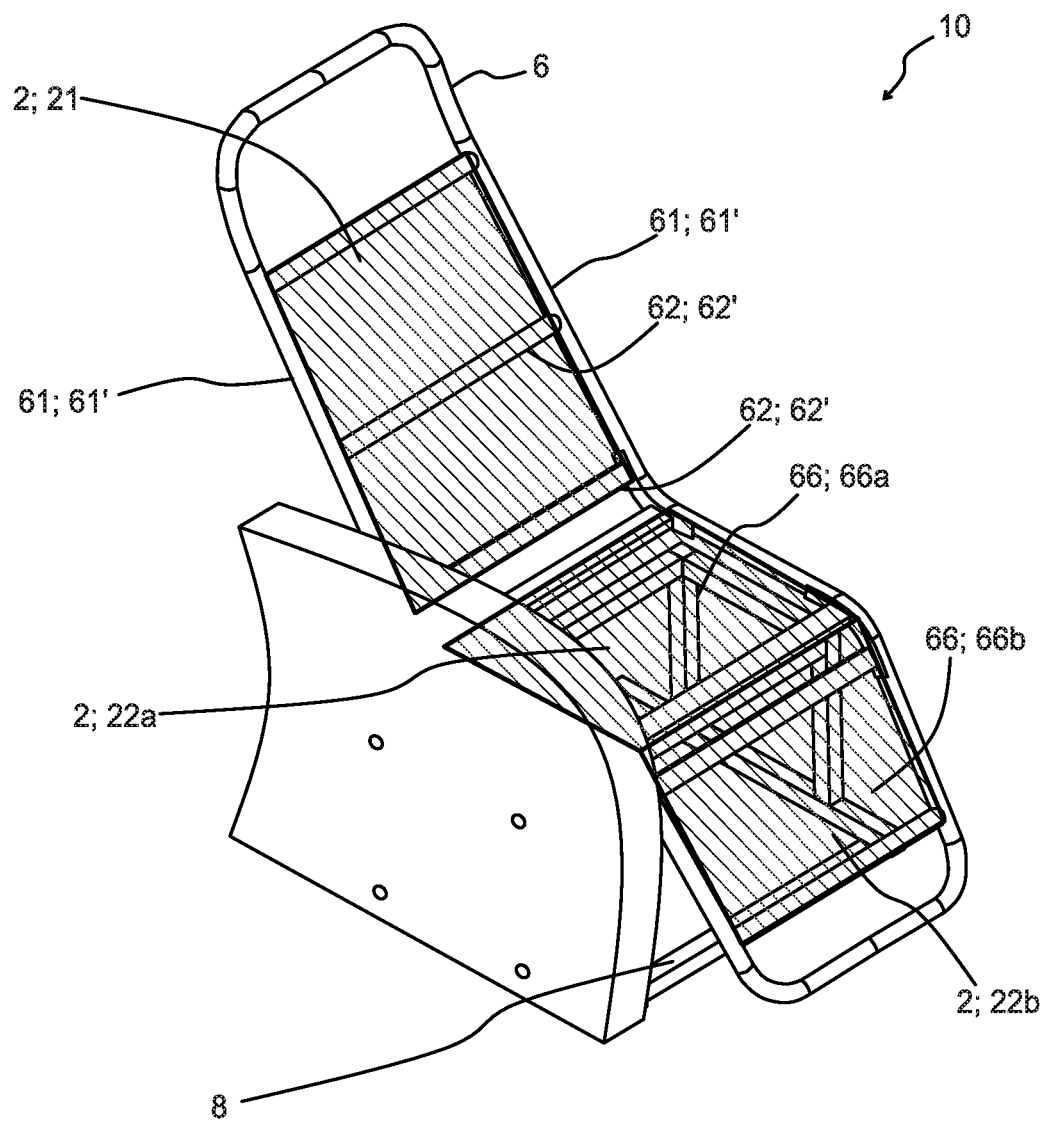
FIGS. 4B and 4C illustrate schematically a base structure for the chair 4A.
Figure 4C:
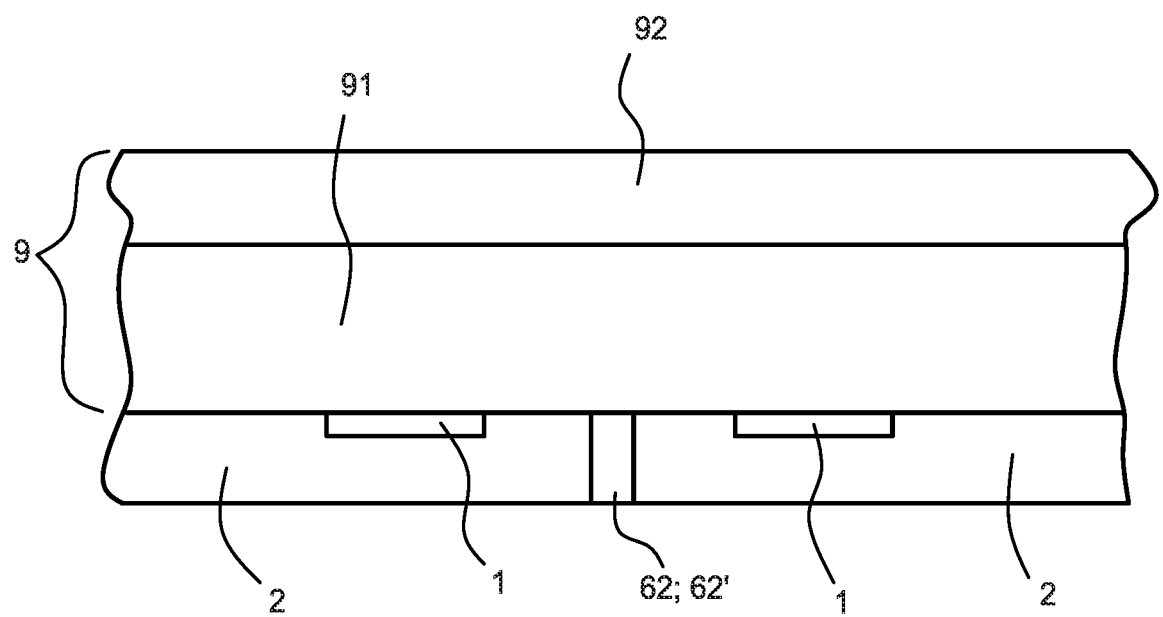

Next will be further described by means of FIGS. 4A-4C a chair according to one exemplary embodiment of the invention, which is equipped with vibrator elements 1.

Visible in FIG. 4A is a chair 7 without a base, upholstery and side supports for clarifying the position of vibrator elements 1 fitted in the chair 7. In FIG. 4B is visible an apparatus 10, comprising the chair 7 of FIG. 4A fitted with side supports and a plate type base 2 without upholstery and vibrator elements. FIG. 4B serves primarily to illustrate a hard base 2, the vibrator elements 1 being embedded in or abutted against its base members 21, 22. FIG. 4C shows in more detail the abutment of vibrator elements 1 on the base member 21 of a back 65 included in the base 2 and the conduction of vibrations by way of upholstery 9 to a target or the body of a user.

The chair 7 visible in FIGS. 4A-4C consists of a planar back 65, which supports the user's back and head and to hose bottom end is connected a two-piece seat 66 that supports the lower limbs. The back 65 and the seat 66 are bordered by a three-piece tubular frame 6, featuring two continuous, approximately co-directional tubes 61; 61' and 61; 61" lengthwise of the chair, between which extend a plurality of thin rungs 62. The frame 6 has its tubes 61 lengthwise of the chair extending in the back 65 in approximately vertical direction or at a slight angle relative to vertical direction and in the upper and lower components of the seat 66 in horizontal direction as well as in approximately vertical direction or at a slight angle relative to vertical direction, respectively.

Accordingly, the longitudinal tubes 61; 61' and 61; 61" of the frame 6 define a longitudinal direction of the seat 66 as well as the back 65, the rungs 62 in turn defining a lateral direction of the seat 66 and the back 65. To the horizontally extending rungs 62 of the seat 66 and the back 65 is fastened a plate type base 2 provided with vibrator elements 1 and consisting of base plates. The chair 7 has its tubular frame 6 fastened to a likewise tube-frame stand 8 resting on a foundation, such as a floor.

The seat 66 consists of two interlinked, planar seat components 66; 66a and 66; 66b; a first upper seat component 66a supporting an upper part (thighs) of the legs and being approximately horizontally directed, as well as a second lower seat component 66b supporting a lower part of the legs and having its longitudinal direction at an angle relative to the longitudinal direction of the first upper seat component 66a supporting the upper part of the legs. Between the seat components 66a and 66b exists a certain distance for avoiding the conduction of vibrations between members of the base.

Inside the back 65, the lower seat component 66b and the upper seat component 66a of the chair 7 extends a continuous or preferably discontinuous stiff plate type base 2 in whose respective base members 21, 22b and 22a, which are located in the back 65, in the lower seat component 66b and in the upper seat component 66a, are embedded nine vibrator elements 1. The vibrator elements 1 are vibrators which convert electronic oscillation into mechanical vibration. Regarding its material, the base 2 is made of a relatively hard stuff, such as wood or metal.

To the stand 8 of the chair 7, below the level of the chair's approximately horizontal seat 66, is attached a signal board 41 as well as an amplifier board/amplifier boards 42 coupled with the signal board. From the amplifier board 42 extends a signal channel 3 to each vibrator element 1 (total of nine signal channels). FIG. 4A shows further a data processing unit 5, which is functionally, such as in a wired manner or wirelessly, in communication with the signal board 41. The data processing unit 5 includes an external programmable oscillator 53, a user interface 51 and a central processing unit 52, as well as a suitable piece of software.

Inside the planar base members of the back 65, the first seat component 66; 66a supporting an upper part of the legs, and the second seat component 66; 66b supporting a lower part of the legs are disposed, respectively, a first group, a second group, and a third group of vibrator elements (1; 1a, 1b, 1c), whereby to each vibrator element 1 extends its designated signal channel 3 from the amplifier board 42 present in connection with the signal board 41. By way of the signal channel 3, each vibrator element 1 is supplied with an impulse train 200, which has been amplitude-modulated by means of the signal board 41 and the amplifier boards 42 coupled therewith, and from which is produced by the vibrator 1 a possibly maximum amplitude-wise fluctuating (amplitude-modulated) pulse train or vibration cycle 1000; 1001, 1002 . . . or 100; 101, 102 . . . of mechanical vibration's first vibration component 1000 or second vibration component 100. As visible in FIG. 4A, the back 65 has its base member 21 provided with two vibrator elements intended for massaging the upper back area and set side by side in a horizontal direction of the back, and the lower back area therebelow is likewise provided with two vibrator elements set side by side in a horizontal direction of the back with one more vibrator element designated for neck massage. The first seat component 66a, supporting an upper part of the user's legs, has its base member 22a provided with two vibrator elements 1 set side by side in a horizontal direction and having a common location with each other in terms of a longitudinal direction of the upper seat component 66a, and the second lower seat component 66b, supporting a lower part of the user's legs, has its base member 22b respectively provided with two vibrator elements 1 set side by side in a horizontal direction and having a common location with each other in terms of a longitudinal direction of the lower seat component.

Each vibrator element embedded within the base member 21, 22 of the apparatus' base 2 is able to bring about a resonance of the base member material surrounding the same. Since each base member is separate from the other base member, the vibrations are not significantly conducted from the first 21 base member to the second base member 22, nor between the base members 22a and 22b supporting the lower limbs.

FIG. 4C shows, from a direction IVC in FIG. 4B, a section view of two base panels 21 included in the base 2 and separated by a rung 62. The base panels 21 have embedded therein two mechanical vibrators 1, such as Bass Pump 3. Above each vibrator 1 is a first and a second cushion layer 9; 91 and 9; 92 which, jointly with a surface material of the chair (leather upholstery or the like), make up a medium along which the vibrations are conducted to various parts of the user's body. Consequently, mechanical vibration is conducted from the mechanical vibrator 1, as well as from the base panel 21 of the back 65, by way of the back, seat cushions and seat upholstery (not shown in the figures) visible in FIG. 4C, to the user's body parts.

The vibrator elements 1 are used for supplying the user's muscles and other body parts with pulse trains or vibration cycles 1000 or 100 included in a first or a second vibration component and comprising low frequency mechanical vibrations, wherein the frequency of each pulse is 20-50 Hz. As mentioned in the discussion of FIG. 1, each pressure pulse 400 of a pulse train has a certain duration t determined on the basis of vibration frequency, as well as the so maximum amplitude Am determined on the basis of signal amplification.

Next, the establishment of a mechanical pulse train 100 is further clarified by referring to FIG. 3, specifically with regard to an apparatus 10 illustrated in FIGS. 4A-4C.

The apparatus 10 according to the invention comprises a data processing unit, is including a user interface 51, a central processing unit 52, as well as means for setting up a signal pulse train 300 on the basis of instructions given by the user. The means for producing a signal pulse train comprise an oscillator 53 as well as an appropriate piece of software. The user operates the user interface 51 to determine, for desired pulse trains 101, 102, 103 . . . or 1001, 1002, 1003 . . . included in a first or a second vibration component of a vibration cycle 100 or 1000 of mechanical vibration, a duration T, a maximum amplitude Am and its possible change, as well as a vibration frequency f and its change from a pulse train to the next, or a minimum and maximum frequency fmin, fmax, as well as a contact power I in decibels with a person's body, and, on the basis of these, the data processing unit 5 is able to generate, through the intermediary of the oscillator 53 and the appropriate piece of software, a control instruction or signal pulse trains 300 which are consistent with these to-be established pulse trains of vibration cycles 100 or 1000 of mechanical vibration. The oscillator 53 and also the appropriate piece of software, both programmable, are able to generate, on the basis of instructions given by the user, signal pulse trains 300 each of which comprises at least a data item regarding the total duration T, possible changes (i.e. amplitude modulations, cf. FIG. 1) in the frequency f as well as in the maximum amplitude and/or maximum vibration pressure Pmax of the pressure pulses 400 of a pulse train contained in each mechanical vibration component of a vibration cycle 100, 1000 over the duration T of the second vibration component 101, 102 . . . or the first vibration component 1001, 1002 . . . .

The programmatically generated signal pulse train 300 is transmitted from the data processing unit 5 to the signal board (board in general 4; signal board 41), which produces a plurality (for example 3 in number) of electrical impulse trains 200 from each pulse signal train 300 on the basis of data contained in the pulse signal train. Each impulse train 200 comprises analog or preferably digital electrical pulse trains having the duration T, in which the power, the strength I or the voltage U of electric current change between a minimum and a maximum and at the same time the frequency F of electric field changes within a certain range.

The impulse train 200, produced and multiplied with the signal board 41, is transmitted to one or more amplifier boards 42 for providing a desired maximum amplitude modulation in a per se conventional manner. Thereafter, each impulse train 200 arriving at the amplifier boards 42 is transmitted in an amplified condition by way of its signal channel 3 to the respective mechanical vibrator element 1. The amplification of electrical analog or digital impulse trains 200, as well as the conversion thereof into a pulse train of a vibration cycle 100 or 1000 of mechanical vibration, is per se known technology for which reference is made to the literature of this field.

In this context, just one exemplary practice will be described for converting an electrical impulse train 200 into a respective mechanical pulse train 100 for a chair 7 depicted in FIGS. 4A-4B. In an apparatus 10 fitted in the chair 7, the signal board 41 is located at a stand 8 of the chair 7 below the level of the upper seat component 66a of the seat 66, and the signal board 41 has three amplifier boards (board in general 4; amplifier board 42) coupled therewith. From each amplifier board 42 extend a plurality of signal channels 3 to the vibrator elements 1. The signal channels 3 communicate the electrical impulse train 200, amplified by the amplifier board 42 (amplitude-modulated), to the mechanical vibrators 1 which generate from the impulse train 200 an amplitude-modulated pulse train of a vibration cycle 100 or 1000 (first vibration component, second vibration component) comprising mechanical vibrations. In one embodiment of the invention, each amplifier board 42 is supplied, as an input signal, with three analog or digital impulse trains 200 from the signal board 41, said impulse trains being then amplified and transmitted by the amplifier board 42 by way of three different signal channels 3 to three mechanical vibrators. The chair shown in FIGS. 4A-4C has nine vibrator elements 1 each of which receives its designated signal channel 3 from three amplifier boards 42.

In one embodiment of the invention, the mechanical vibrator 1 applies the same principle as described in socalled "vibration speaker" devices. Such is for example the "bass pump 3" used as a vibrator element in the chair of FIGS. 4A-40, wherein electrical vibration is converted into mechanical vibration.

In one embodiment of the invention, the vibrator elements 1, embedded in the respective base members 21, 22a of the chair's back 65 and upper component 66a of its seat 66, are used to transmit pulse trains (sound waves) of about 20-40 Hz, preferably 23-34 Hz, included in the first vibration component of mechanical vibrations and remaining constant in terms of their frequency f, to the user's back area and his/her area of thigh muscles. The maximum amplitude Am of these vibrations remains constant during one pulse train or each vibration cycle 1000; 1001, 1000; 1002, 1000; 1003 . . . , but changes when proceeding from a vibration cycle to the next.

In one implementation of the invention, any vibrator element 1 of the back or the seat is used for supplying the body's muscles/muscle groups with low frequency pulses of for example 25 Hz, included in mechanical vibrations and remaining constant in terms of their frequency f. Such a pulsating vibration has been found to possess excellent soothing effects.

In addition, a lower part or calves of the legs, a lower part of the shins and the ankle muscles of the user will be supplied with low frequency second pulse trains of about 20-50 Hz, i.e. second vibration cycles 100, included in mechanical vibrations and fluctuating in terms of their frequency. The pulse trains are generated by vibrator elements 1 embedded in the base member 22b of the lower seat component 66b.

It is obvious for a skilled artisan that the invention described above by way of working examples can be varied within the scope of an inventive concept presented in the claims.

Hence, in a preferred embodiment of the invention, the chair has its back provided with just two vibrator elements 1, one for the lower back and one for the upper back.

In another preferred embodiment of the invention, the chair 7 does not have so inside its frame 6 an actual solid base member 21, 22, but the base member/base members is/are made up of a mattress inside which the vibrator elements 1 are embedded. The mattress is additionally topped with leather upholstery or the like cushioning from which vibration is conducted to a part of the user's body.

In yet another preferred embodiment of the invention, the chair 7 has its back 65 lowered for the duration of a treatment to a certain low angle 0-40 relative to the seat member 66.

Next clarified with examples will be a method of the invention as well as use of the apparatus 10. The apparatus employed in the examples was an apparatus 10 illustrated in FIGS. 4A-4C and fitted in the chair 7.

EXAMPLES

1) Sleep Program

The vibrator elements of the chair 7 were used to generate mechanical vibration (pressure waves) of about 25-34 Hz in terms of its frequency, which was transmitted by way of the body parts-matching base members 9 of the chair 7 to the users' body parts: neck, back, thighs and calves.

The first vibration component of low frequency vibration consisted of a plurality of successive vibration cycles 1000; 1001, 1000; 1002, 1000; 1003 each having a duration T; T1, T; T2, T; T3 . . . of about 4 min 45 seconds, except for the vibration cycle 108 which lasted 4 min 15 seconds. Hence, the vibration cycles of the first vibration component had a total duration Tall T1+T2+T3 . . . .

Within each vibration cycle 1000; 1001, 1000; 1002, 1000; 1003 of the first vibration component the vibration frequency f remained constant fa, fb, fc, fd, yet fluctuated between successive vibration cycles in a linear manner within the range of 25-34 Hz. Within each pulse train it was possible to use amplitude modulation of the maximum amplitude Am or to keep the maximum amplitude Am constant. Amplitude pulses endure always about 10 seconds. At the onset of an amplitude pulse, the amplitude A rose from zero to maximum value Am in 2.7 seconds, remained at maximum Am for 3.2 seconds, and fell to zero in 4.3 seconds. Between amplitude pulses may exist short pauses. Power I of the first vibration component was measured at a folding point between the leg member and the back member, at which point develops the highest vibration pressure. The measurement was conducted at a height of about 5 cm from the chair surface, i.e. the employed medium was air. The measurement was conducted with Benetech GM 1351 sound level meter.

| Pulse train 1000 | constant frequency f/Hz | power I/dB |
|---|---|---|
| 1001 | 25 | 51-59 |
| 1002 | 26 | 50-58 |
| 1003 | 27 | 49-58 |
| 1004 | 28 | 51-60 |
| 1005 | 29 | 52-60 |
| 1006 | 30 | 50-59 |
| 1007 | 31 | 52-61 |
| 1008 | 34 | 55-64 |

After this, in each pulse train 1009 . . . 1016 the constant frequency was maintained in such a way that the constant frequency in turn declined from frequency 34 Hz (pulse train 1009) to frequency 25 Hz (pulse train 1016) in the corresponding manner.

As can be seen from the above fluctuations of constant frequencies fa, fb, fc. from a pulse train to the next (from a vibration cycle to the next), the change of constant frequencies is monotonous and mainly linear, i.e. in a group of successive vibration cycles the vibration frequency rises 1-4 Hz or falls 1-4 Hz.

The power (I) of vibration at a person's body was measured with decibel measurements by using a Benetech sound level meter. Since the measured power in decibels depends on the presently existing frequency level of sound, it was in the first vibration component that a part of the body (here the leg member or the back member) was subjected to a relatively high vibration power, which was within the range of 49-64 dB, since the vibration was of a low frequency.

After this, the vibrator elements of the chair 7 were used to generate a second vibration component 100 of about 23-33 in terms of its frequency, which comprised one massaging vibration cycle lasting about 3-4 seconds and comprising mechanical vibration (pressure waves) transmitted by way of the body parts-matching base members 9 of the chair 7 to the users' body parts: neck, back, thighs and calves. A contact power I (dB) for the vibration cycle of the second vibration component 100 with the user's back and leg part was measured the same way as earlier for the first vibration component's vibration cycles and it was found to fluctuate within the range of 57-64 dB.

The vibration frequency fluctuated in this second vibration component within the range of 23-33 Hz, the frequency fluctuation occurring in the second vibration component's vibration cycle in the shape of a sine curve over the duration of 6.3 seconds. During each frequency pulse, the frequency f changed from 23 Hz first to 33 Hz and then back to 23 Hz. This second vibration component (pulse train) contained additionally amplitude modulation, such that the amplitude pulse 400 of each pulse train 100 had a duration t of about 1 second, whereby the maximum amplitude changed from 0 to Am in 0.3 seconds, remained at the maximum for 0.3 seconds, and then fell to zero in 0.3 seconds.

In the invention, various parts of the body are generally supplied with vibration cycles identical in terms of their basic vibration, but the maximum amplitude Am, and thereby the contact power I of vibration with a part of the body, will be changed. Typically, vibration cycles can be transmitted to the calves with the highest contact power, to the back and thighs with a slightly lower and to the neck with the lowest power.

2) Assessment of Stress-Related Sleep Disorders and Difference Made by a Method of the Invention in Stress-Related Sleep Disorders In an effort to study stress-related transient sleep disorders, as well as sensations of anxiety associated with sleep disorders, the stress-related sleep disorder in test persons was surveyed by means of several written questionnaire studies (Helsinki Sleep Clinic, Research Center Vitalmed, private survey). The questionnaire study was used to find out the presence of transient stress-related insomnia and the degree of severity of insomnia. In the questionnaire study, those persons were excluded with who the sleep disorder stemmed from something other than stress, such as from the restless legs syndrome, sleep apnea, or MS disease Aspects regarding the length and quality of sleep were monitored with a written PSQI (Pittsburgh Quality Index questionnaire).

Aspects regarding the severity of insomnia were in turn monitored with a written ISI questionnaire (Insomnia Severity Index questionnaire).

On the basis of what was uncovered in the questionnaire study, it was evaluated whether a test person was probably suffering from a transient stress-related sleep disorder. Test persons with a likelihood of having a stress-related sleep disorder were exposed to mechanical vibration, generated by the above-described chair 7, by transmitting to the test person's body or selected body parts mechanical vibration which included a first vibration component and a second vibration component for thirty-nine minutes.

After the body of test persons had been exposed to mechanical vibration possessing first and second vibration components, a re-observation was conducted regarding the level of stress-related sleep disorder. The observation was conducted with a movement activity-measuring, portable actigraph unit, a blood pressure measurement, a heart rate measurement, a written questionnaire study, sleep diary, or a combination thereof.

Based on the study, the severity degree of insomnia experienced by test persons declined (more severe insomnia scores more points) and at the same time the quality of sleep and the perception of anxiety declined in a statistically significant manner.

3) Assessment of Stress Level and Difference Made by a Method of the Invention in Stress Level In the stress/sleep study of Heli Haapaniemi, the body or selected parts of the body of test persons were exposed four times to mechanical vibration of the invention with first and second vibration components by using, in order to generate the vibration, an apparatus as defined in an arrangement of the invention, wherein the apparatus is fitted in the chair 7. The exposure times were followed by a re-observation of the stress-related sleep disorder level and the observation was conducted by using e.g. a heart rate variability measurement as well as a measurement for the level of stress hormones. Heart rate variability measuring devices are plentiful in the market and the measuring method has been standardized.

Heart rate variability is generally comparable with stress level, which in general supports changes occurring in the level of stress. The heart rate variability analysis was conducted with the Kubios software from which were selected five parameters used as basis for studying changes occurring in heart rate variability. These parameters are Mean RR, STD RR, RMSSD, LF and HF. In summary, it can be said that a majority of test persons showed observable clear changes in stress and sleep disorder levels as a result of the method. The changes were visible as the alleviation of stress level and the increase of general relaxation level along with chair therapies administered by the method. Each person is affected by the method individually but, based on the results, the method had beneficial effects also on the activity of the autonomic nervous system, i.e. the function of the parasympathetic nervous system became more active.

The level of stress hormones was measured by salivary cortisol determinations. These were conducted with a radioimmunoanalysis method by using a test kit manufactured by Orion. The results of salivary cortisol samples were compared to reference ranges provided by Orion, the afternoon values of which were 0.6-4.9 nmol/l.

Even though the test cycle only included four chair therapy sessions without a therapeutic dialogue intervention, the final results in a majority of test persons were good.

The invention claimed is:

1. A method for alleviating a person's stress-related transient adjustment insomnia, said stress-related transient insomnia comprising at least one of:
   temporary and short-term adjustment insomnia, which in international sleep disorder classification has been categorized in class F51.0;
   transient stress-related sleeplessness, which is included in adjustment insomnia and which lasts a few nights;
   jet lag-related sleep disorders, which in the international sleep disorder classification have been categorized in class Z58.8, and
   shift work-related sleep disorders, which in the international sleep disorder classification have been categorized in class G47.2; the method comprising:
applying low frequency vibration to the person's body or a selected part of the body with an apparatus which includes a base member and mechanical vibrators coupled to signal sources by which said base member is set in vibration, wherein said applying comprises:
using said mechanical vibrators and said signal sources to set the base member in vibration in such a way that one of its surfaces transmits mechanical vibration, wherein said mechanical vibration comprises a plurality of mechanical vibration pulse trains which are conducted to the person's body or selected body part, wherein successive ones of said mechanical vibration pulse trains to be transmitted to the body or the selected part of the body comprise
   a first vibration component, which comprises a plurality of first successive pulse trains or vibration cycles transmitted at successive time periods to the body or said part of the body, each of said first successive pulse trains or vibration cycles having a duration of more than one minute and a constant frequency within a range of 20-50 Hz through said duration of the first successive pulse trains or vibration cycles, while the first vibration component is at the same time adapted to be such that pressure pulses included in each of said first successive pulse trains or vibration cycles have a contact power with the body or said body part within a range of 40-70 dB, whereby the constant frequencies of successive ones of the first successive pulse trains or vibration cycles are mutually different and change monotonously and linearly when proceeding from a first one of said first successive pulse trains or vibration cycles to a second one; and further
   a second vibration component, which comprises at least one second pulse train or vibration cycle transmitted to the body or said part of the body, wherein pressure pulses included in the at least one second pulse train or vibration cycle have a frequency fluctuating within a range of 20-50 Hz, over a course of 2-10 seconds, and said frequency of the pressure pulses included in the at least one second pulse train or vibration cycle changes in accordance with a sine, triangle or square wave.

2. The method according to claim 1 wherein, in the first successive pulse trains or vibration cycles of the first vibration component, a fluctuation of a maximum amplitude (Pmax1, Pmax2) of successive pressure pulses of mechanical vibration generates sine wave-shaped amplitude pulses whose maximum amplitude (Am) either remains constant during each individual one of said first successive pulse trains or vibration cycles but changes between two successive ones of said first successive pulse trains or vibration cycles, or fluctuates during each individual one of said first successive pulse trains or vibration cycles.

3. The method according to claim 2, wherein the maximum amplitude of successive pressure pulses contained in each said second pulse train or vibration cycle of the second vibration component changes in 5-20 seconds, in a manner consistent with a sine wave.

4. The method according to claim 1, further comprising detecting a severity of the person's stress by measuring the person's blood pressure or heart rate.

5. The method according to claim 1, further comprising detecting a severity of the person's stress by assessing the person's sentiments of stress or by measuring the amount of hormones associated with stress level, the hormones including at least one of serotonin, dopamine, melatonin, cortisol, histamine or gamma-aminobutyric acid (GABA), and using the measured amount of hormones as an indicator of the severity of the person's stress.

6. The method according to claim 1, wherein the first or second successive pulse trains or vibration cycles of the first and second vibration components respectively comprise pressure pulses of longitudinal vibration, which are generated in a solid medium and each of which has a contact power with a part of the body within the range of 40-70 dB.

7. The method according to claim 6, wherein the constant frequencies of the first successive pulse trains or vibration cycles of the first vibration component change monotonously from one of said first successive pulse trains or vibration cycles to another one of said first successive pulse trains or vibration cycles, whereby the constant frequencies of two successive ones of said first pulse trains or vibration cycles have a difference of 1-4 Hz.

8. The method according to claim 1, wherein the frequency of successive pressure pulses of the at least one second pulse train or vibration cycle of the second vibration component fluctuates in a manner of a sine wave within the range of 20-50 Hz, whereby the difference between a minimum and a maximum frequency within each individual frequency pulse is 6-10 Hz.

9. The method according to claim 8, wherein a maximum amplitude of the successive pressure pulses of the at least one second pulse train or vibration cycle of the second vibration component also changes in a manner of a sine wave over a period of about 1-2 seconds within a range of 0-Amax, wherein Amax is a maximum amplitude corresponding to a maximum pressure difference of the pressure pulse with a largest amplitude of said successive pressure pulses.

10. The method according to claim 8, wherein the pressure pulses contained in the at least one second pulse train or vibration cycle have an amplitude (A) such that said pressure pulses have a contact power (I) with a person's body within a range of 40-70 dB.

11. A method for reducing a person's stress by applying low frequency vibration to person's body or to at least one part of the body with an apparatus which includes a base member and mechanical vibrators coupled to signal sources by which said base member can be set in vibration, said method comprising using said mechanical vibrators, and said signal sources to set the base member in vibration in such a way that one of its surfaces transmits mechanical vibration, comprising a plurality of mechanical vibration pressure pulse trains which are conducted to the person's body or selected body part, wherein successive ones of said mechanical vibration pressure pulse trains to be transmitted to the body or a selected part of the body comprise:
 a first vibration component, which comprises a plurality of first successive pulse trains or vibration cycles transmitted at successive time periods to the body or a selected part of the body, each of said first successive pulse trains or vibration cycles having a duration of more than one minute and a constant frequency within a range of 20-50 Hz through said duration of the pulse train or vibration cycle, while pressure pulses of the first vibration component are at the same time adapted to be such that the pressure pulses included in each of said first successive pulse trains or vibration cycles have a contact power with the body or said body part within a range of 40-70 dB, whereby the constant frequencies of successive ones of the first successive pulse trains or vibration cycles are mutually different and change monotonously and linearly when proceeding from a first one of said first successive pulse trains or vibration cycles to a second one; and further
 a second vibration component, which comprises at least one second pulse train or vibration cycle transmitted to the body or said part of the body, wherein pressure pulses included in the at least one second pulse train or vibration cycle have a frequency fluctuating within a range of 20-50 Hz, over a course of 2-10 seconds, and said frequency change of the pressure pulses included in the at least one second pulse train or vibration cycle occurs in accordance with a sine, triangle or square wave.

12. An arrangement for alleviating a person's stress-related transient adjustment insomnia with an apparatus which comprises a plurality of mechanical vibrators mounted on a first side of one or more solid or flexible resonatable base members said mechanical vibrators being capable of converting an electrical impulse into a pulse of mechanical vibration, as well as a data processor with a capability of producing a control instruction for setting up an electrical impulse train for use by the mechanical vibrators for setting the one or more solid or flexible resonatable base members h to vibrate in resonance with said mechanical vibrators in such a way that a second surface of the one or more solid or flexible resonatable base members, which is opposite to said first side and closer to a person's body, transmits to the body or to a selected part of the body low frequency mechanical vibration that comprises successive pressure pulses, wherein the pressure pulses make up:
 a first vibration component, which comprises a plurality of successive soothing pulse trains or vibration cycles transmitted to the body or said part of the body at successive time periods, which comprises low frequency successive pressure pulses, each of said soothing pulse trains or vibration cycles having a duration of more than one minute and a vibration frequency which is constant within a range of 20-50 Hz through said duration of the soothing pulse train or vibration cycle, while the low frequency successive pressure pulses of the first vibration component are at the same time adapted to be such that the low frequency successive pressure pulses included in each of said soothing pulse trains or vibration cycles have a contact power (I) with said body part within a range of 40-70 dB, and
 a second vibration component, which is transmitted thereafter to the body or to said part of the body and which comprises at least one second massaging pulse train or vibration cycle, pressure pulses included in said second vibration component having a frequency fluctuating within a range of 20-50 Hz, over a course of 2-10 seconds, and said frequency of the pressure pulses changing in accordance with a sine, triangle or square wave.

13. The arrangement according to claim 12, wherein the apparatus is a bed or chair, the mechanical vibrators mounted on the one or more solid or flexible resonatable base members of the apparatus being located inside a frame of the chair or bed, and mechanical vibrations generated by the mechanical vibrators are adapted to be conducted by way of a medium made of leather and/or cushioning to the person's body or selected part of the body desired to have vibration applied thereto.

14. The arrangement according to claim 13, wherein the apparatus is the chair, wherein the chair includes a back and a two-piece seat which comprises an upper seat component adapted to support an upper part of legs and having an approximately horizontal orientation as well as a lower seat component adapted to support a lower part of the legs and having a longitudinal direction at an angle relative to a longitudinal direction of the upper seat component, whereby inside the back, the lower seat component and the upper seat component of the chair there extends a discontinuous stiff base whose respective parts constitute said one or more solid or flexible resonatable base members, which are located in the back, in the lower seat component and in the upper seat component and which have embedded therein at least one of said mechanical vibrators.

15. The arrangement according to claim 12, wherein said apparatus further comprises a central processor and means for setting up a signal pulse train on the basis of instructions given by the user.

16. The arrangement according to claim 15, wherein the data processing unit is adapted to generate, by means of an oscillator, a control instruction, that comprises the signal pulse train, said data processing unit is functionally coupled with an analog or digital signal board attached to the apparatus' base, said signal board being in turn adapted to convert the signal pulse train arriving from the data processor into a respective electrical analog or digital impulse train, and an amplifier board by which the electrical analog or digital impulse train departing from the signal board configured to be amplified and delivered to a desired mechanical vibrator of said mechanical vibrators by way of an appropriate signal channel for generating mechanical vibration.

17. A piece of software installed in a data processing unit and adapted to generate, when executed by a central processing unit, a control instruction that comprises, a signal pulse train with a capability of generating, when coupled to one or more mechanical vibrators, a plurality of mechanical vibration pulse trains, said mechanical vibration pulse trains comprising:

a first vibration component, which comprises a plurality of first successive pulse trains or vibration cycles transmitted at successive time periods to a part of a body, each of said first successive pulse trains or vibration cycles having a duration of more than one minute and a constant frequency within a range of 20-50 Hz through said duration of the pulse train or vibration cycle, while the first vibration component is at the same time adapted to be such that pressure pulses included in each of said first successive pulse trains or vibration cycles have a contact power (I) with the body or the selected body part within a range of 40-70 dB, whereby the constant frequencies of successive ones of the first successive pulse trains or vibration cycles are mutually different and change monotonously and linearly when proceeding from a first one of said pulse trains or vibration cycles to a second one; and a second vibration component, which comprises at least one second pulse train or vibration cycle transmitted to said part of the body, wherein the pressure pulses included in the at least one second pulse train or vibration cycle have a frequency fluctuating within a range of 20-50 Hz over a course of 2-10 seconds, and said frequency of pressure pulses included in the at least one second pulse train or vibration cycle changes in accordance with a sine, triangle or square wave.

* * * * *